United States Patent
Wool

(10) Patent No.: US 6,811,397 B2
(45) Date of Patent: Nov. 2, 2004

(54) THREE SEGMENT ORTHODONTIC ARCH WIRE HAVING UNIFORM FLEXURAL RIGIDITY

(76) Inventor: Arthur L. Wool, 1402 Penn Ave., Wyomissing, PA (US) 19610

( * ) Notice: Subject to any disclaimer, the term of this patent is extended or adjusted under 35 U.S.C. 154(b) by 0 days.

(21) Appl. No.: 10/214,601

(22) Filed: Aug. 9, 2002

(65) Prior Publication Data

US 2004/0029067 A1 Feb. 12, 2004

(51) Int. Cl.$^7$ ................................................ A61C 7/00
(52) U.S. Cl. ............................................... 433/20
(58) Field of Search ............................ 433/20, 21, 22, 433/7, 18

(56) References Cited

U.S. PATENT DOCUMENTS

| | | |
|---|---|---|
| 4,412,819 A | 11/1983 | Cannon |
| 4,424,033 A | 1/1984 | Wool |
| 5,131,843 A * | 7/1992 | Hilgers et al. ................ 433/20 |
| 5,174,753 A | 12/1992 | Wool |
| 5,722,827 A | 3/1998 | Allesee et al. |
| 5,882,193 A * | 3/1999 | Wool ............................ 433/20 |
| 5,910,008 A * | 6/1999 | Tran ............................. 433/22 |
| 6,036,489 A | 3/2000 | Brosius |

* cited by examiner

Primary Examiner—Kevin Shaver
Assistant Examiner—Melba Bumgarner
(74) Attorney, Agent, or Firm—Antonelli, Terry, Stout & Kraus, LLP

(57) ABSTRACT

An orthodontic arch wire has a generally parabolic shape. The arch wire includes a curved anterior segment and a pair of posterior segments connected to and extending from respective ends of the curved anterior segment. The curved anterior segment and the pair of posterior segments comprise three discrete pieces having substantially the same flexural rigidity. The three pieces are joined together to form the generally parabolic shape.

16 Claims, 2 Drawing Sheets

THREE SEGMENT ORTHODONTIC ARCH WIRE HAVING UNIFORM FLEXURAL RIGIDITY

BACKGROUND OF THE INVENTION

The present invention relates to an orthodontic arch wire.

A variety of malocclusions are corrected by the use of orthodontic arch wires. In corrections using arch wires, brackets are secured to the patient's teeth and, in each of a number of stages during the course of treatment, an arch wire is secured in the brackets. As treatment progresses, the arch wire which is used more closely approaches the ideal arch form. The arch wires progressively correct misalignments of the patient's teeth.

It is known in the art to use an arch wire of non-circular cross-section, e.g., rectangular or trapezoidal, in brackets with rectangular slots so that the arch wire cannot rotate in the slot and that torque can be applied to the teeth by the arch wire through the brackets. One problem with the use of non-circular cross-sectional arch wires is that the arch wire tends to bind in the brackets on the posterior teeth as a result of excessive friction. It is known from my prior U.S. Pat. No. 4,424,033, the contents of which are incorporated by reference herein in their entireties, to use an arch wire having posterior segments of circular cross-section and an anterior segment, at least a part of which is rectangular or trapezoidal in cross-section. The arch wire described in my prior U.S. Pat. No. 4,424,033 has a unitary construction, i.e., is formed from a single or unitary length of wire. Manufacture of such a wire has proved difficult in that it is generally necessary to start with an arch wire of non-circular, e.g., rectangular or trapezoidal, cross-section, and work the posterior segments of the wire to provide a circular cross-section.

It is known from U.S. Pat. No. 4,412,819 to Cannon to provide an orthodontic arch wire formed by uniting a central segment of relatively resilient wire with end or posterior segments of a different and more rigid wire to provide an arch wire having an anterior segment made of a material having a flexural rigidity which is lower than the flexural rigidity of the material forming the posterior segments. The contents of U.S. Pat. No. 4,412,819 to Cannon are incorporated herein by reference in their entireties. However, an arch wire having a more resilient anterior segment is advantageous only in early arch treatment placements when irregular anterior teeth would benefit from being more easily attached to the arch. Moreover, using a resilient anterior segment tends to cause constriction of posterior dental elements. For example, if a resilient Ni—Ti anterior segment is used with elastic pull bilaterally, the anterior radius tends to become V-shaped, constricting the posterior segments. Moreover, the use of dissimilar metals for the anterior and posterior segments makes it difficult to solder or braze the segments together or to a joining element since different fluxes and solders are required for the different metals. Finally, it is often desirable to provide a metal (e.g., gold) plating on the arch wire, this is difficult to do when dissimilar metals are used since the conditioning acids or other baths needed to activate the metal surfaces are different for different metals.

SUMMARY OF THE INVENTION

The present invention concerns an orthodontic arch wire that has a generally parabolic shape. The arch wire includes a curved anterior segment and a pair of posterior segments connected to and extending from respective ends of the curved anterior segment. The curved anterior segment and the pair of posterior segments comprise three discrete pieces having substantially the same flexural rigidity. The three pieces are joined together to form the generally parabolic shape.

DETAILED DESCRIPTION OF THE INVENTION

Figure 1:
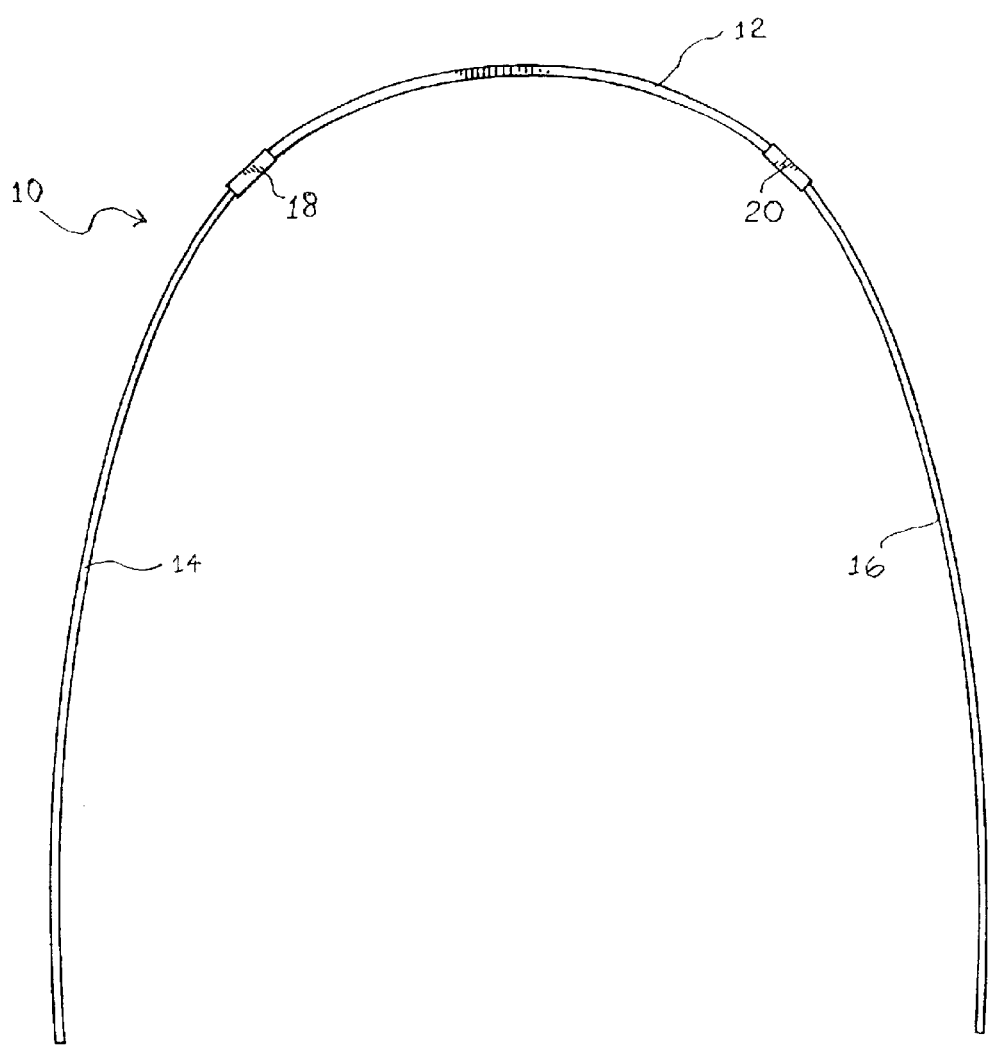
FIG. 1 is a plan view of the orthodontic arch wire of the present invention.

FIG. 1 is a plan view of the orthodontic arch wire of the present invention. As can be seen in FIG. 1, the orthodontic arch wire, generally designated by the reference numeral 10, has a generally parabolic shape. The arch wire 10 includes a curved anterior segment 12 and a pair of posterior segments 14, 16 connected to and extending from the respective ends of the curved anterior segment 12. In the embodiment shown in FIG. 1, the three pieces, i.e., the anterior segment 12 and the pair of posterior segments 14, 16, are joined together to form the generally parabolic shape by tubes 18, 20, respectively, as will be described more fully hereinafter.

The curved anterior segment 12 and the pair of posterior segments 14, 16 comprise three discrete pieces having substantially the same flexural rigidity. The term "flexural rigidity" is used herein in the same manner as in U.S. Pat. No. 4,412,819 to Cannon, i.e., in a conventional sense as defined by Young's modulus of the segment times the second moment of inertia of the segment cross-section. By the term "substantially the same" applicant generally means flexural rigidity which is either identical or varies only to such an extent that the difference has no material effect on the treatment. For example, due to manufacturing tolerances, the segments, even if made nominally of the same alloy, might have slightly different flexural rigidity if manufactured at different times. The term "substantially the same flexural rigidity" is intended to cover different pieces made of nominally the same alloy but, due to manufacturing tolerances, having slightly different, e.g., within a range of 1–3%, flexural rigidity.

Figure 2:
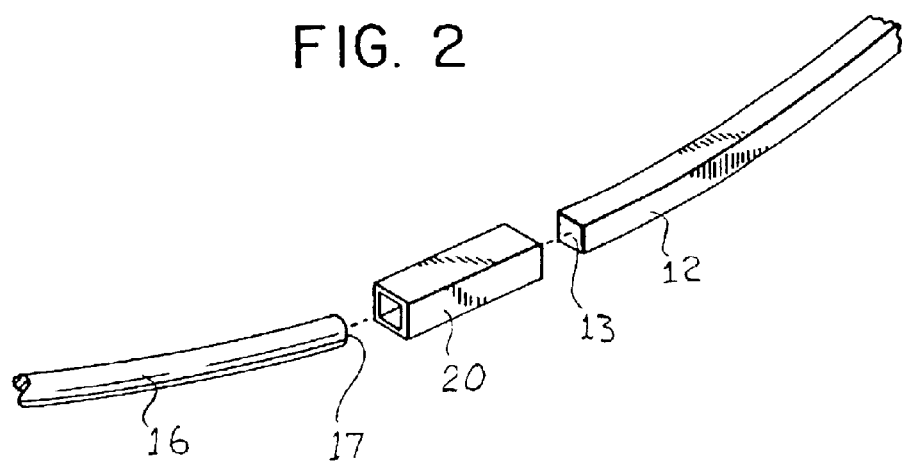
FIG. 2 is an exploded perspective view of one embodiment of the arch wire of the present invention.

The three pieces, i.e., the anterior segment 12 and the posterior segments 14, 16, can be joined together by any method conventionally used in the art to join arch wire segments or join attachments such as hooks to arch wires. In the embodiments shown in the figures, tubes 18, 20 are used to join the segments. As shown in FIG. 2, a hollow tube 20, in this embodiment having a square cross-section, joins the end 13 of the anterior segment 12 to the end 17 of the posterior segments 16. The ends 13 and 17 are inserted and held in the tube 20. In this embodiment, the ends 13, 17 can be butted to one another, although it is also possible to overlap the ends 13, 17 either in the horizontal or vertical direction. Joining can be accomplished by crimping the tube 20, swaging the tube 20, brazing the ends 13, 17 to the tube 20 or to each other soldering the ends 13, 17 to the tube 20 or to each other or welding the ends 13, 17 to the tube 20 or to each other. Laser or spot welding can be used. It may be desirable to use a solderable shrink sleeve applied to the ends 13, 17 before being inserted in the tube and then soldering.

While the tube 20 is shown to have a square cross-sectional shape, the tube can have an oval, round or rectangular cross-sectional shape. Depending on the metal used for the arch wire 10, the respective ends may also be directly soldered or welded without the use of the tube 20.

The anterior segment 12 and the posterior segments 14, 16 have substantially the same flexural rigidity. This is most easily achieved by making the pair of posterior segments 14, 16 and the anterior segment 12 of the same material. The material of which the segments are made can be any material known in the art for arch wires, for example, nickel-titanium alloys (Nitonal), stainless steel, nickel-cobalt alloys (Elgiloy), beta-titanium, etc.

In the embodiment shown in FIG. 2, the anterior segment 12 has a non-circular cross-section while the posterior segment 16 has a circular cross-section. In the embodiment shown in FIG. 2, the anterior segment 12 has a rectangular, e.g., square, cross-section, although other non-circular cross-sections, e.g., trapezoidal, may be used.

Figure 3:
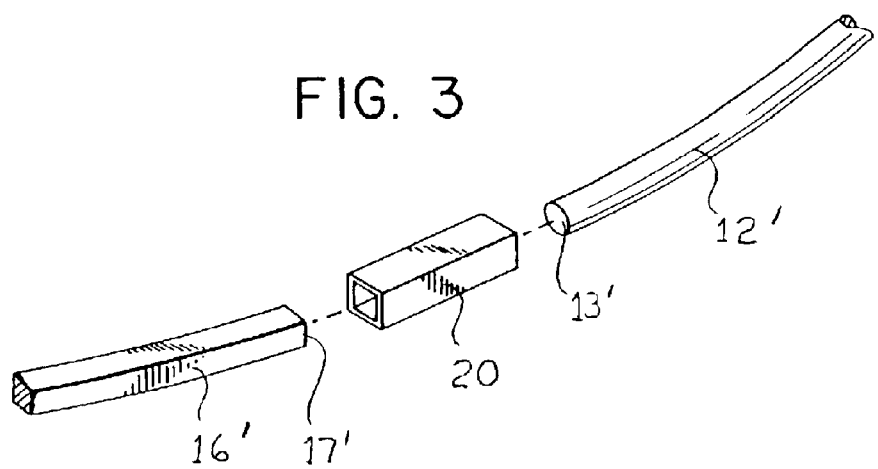
FIG. 3 is an exploded perspective view of another embodiment of the arch wire of the present invention.

In another embodiment shown in FIG. 3, the anterior segment 12' has a circular cross-section while the posterior segment 16' has a non-circular, in this case rectangular, e.g., square, cross-section. This embodiment is useful to apply torque to the posterior teeth without applying them to the anterior teeth. In this embodiment, either or both of the posterior segments may have a non-circular cross-section.

The segment of the arch wire 10 that has the non-circular cross-section can have torque built into it either uniformly over its length or torque which varies over its length. Providing built-in torque is described in U.S. Pat. No. 5,722,827 to Allesee et al and U.S. Pat. No. 6,036,489 to Brosius, the contents of both of which are incorporated herein by reference in their entireties.

It may be desirable for reasons of aesthetics or other reasons, e.g., to lower friction, to plate the arch wire 10 with a metal layer, e.g., a noble metal layer, e.g., gold.

Figure 4:
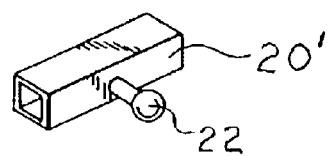
FIG. 4 is a perspective view of a variant of the tube which can be used to join the segments of the arch wire of the present invention.

Either or both the tubes can be provided with an attachment device for various auxiliaries such as elastomerics, elastics, coiled springs, etc. For example, as shown in FIG. 4, a tube 20' is provided with a post or hook 22.

As will be apparent to those skilled in the art, various modifications of the disclosed embodiments could be made without departing from the teachings of the present invention.

I claim:

1. An orthodontic arch wire having a generally parabolic shape, comprising:
    a curved anterior segment; and
    a pair of posterior segments connected to and extending from respective ends of the curved anterior segment;
    wherein the curved anterior segment and the pair of posterior segments comprise three discrete pieces having substantially the same flexural rigidity joined together to form the generally parabolic shape wherein at least one of the three discrete pieces has at least one property other than flexural rigidity different than at least one other of the three discrete pieces.

2. The orthodontic arch wire according to claim 1, wherein each of the pair of posterior segments is connected to one of the respective ends of the curved anterior segment by a tube into which a mating end of the posterior segment and the mating one of the respective ends of the curved anterior segment are inserted and held.

3. The orthodontic arch wire according to claim 2, wherein the mating end of the posterior segment and the mating one of the respective ends of the curved anterior segment are held in each tube by at least one of crimping the tube, swaging the tube, brazing the ends to the tube, soldering the ends to the tube and welding the ends to the tube.

4. The orthodontic arch wire according to claim 2, further comprising a post or hook connected to the tube.

5. The orthodontic arch wire according to claim 1, wherein the pair of posterior segments and the curved anterior segment are made of the same material.

6. The orthodontic arch wire according to claim 5, wherein the pair of posterior segments and the curved anterior segment are made of a material selected from the group consisting of stainless steel, a nickel-titanium alloy, a nickel-cobalt alloy, and beta-titanium.

7. The orthodontic arch wire according to claim 1, wherein the at least one property is cross-sectional shape and wherein the pair of posterior segments have a different cross-sectional shape than the curved anterior segment.

8. The orthodontic arch wire according to claim 7, wherein each of the pair of posterior segments has a circular cross-sectional shape and the curved anterior segment has a non-circular cross-sectional shape.

9. The orthodontic arch wire according to claim 8, wherein the curved anterior segment has a rectangular or trapezoidal cross-sectional shape.

10. The orthodontic arch wire according to claim 8, wherein the curved anterior segment has built-in uniform torque over its length.

11. The orthodontic arch wire according to claim 8, wherein the curved anterior segment has built-in torque that varies over its length.

12. The orthodontic arch wire according to claim 7, wherein each of the pair of posterior segments has a non-circular cross-sectional shape and the curved anterior segment has a circular cross-sectional shape.

13. The orthodontic arch wire according to claim 12, wherein each of the pair of posterior segments has a rectangular or trapezoidal cross-sectional shape.

14. The orthodontic arch wire according to claim 1, further comprising a metal layer plated over the outer surfaces of the arch wire.

15. The orthodontic arch wire according to claim 14, wherein the metal layer plated over the outer surfaces of the arch wire comprises a noble metal.

16. The orthodontic arch wire according to claim 14, wherein the metal layer plated over the outer surfaces of the arch wire is gold.

* * * * *